US012806141B2

(12) United States Patent
Sabir et al.

(10) Patent No.: US 12,806,141 B2
(45) Date of Patent: Nov. 24, 2026

(54) METHODS OF CREATING A SLURRY USING LIPOSOME EMULSIONS

(71) Applicant: Brixton Biosciences, Inc., Cambridge, MA (US)

(72) Inventors: Sameer Sabir, Arlington, MA (US); Charles Sidoti, Boston, MA (US); Olivier Kagan, Belmont, MA (US); Mansoor M. Amiji, Attleboro, MA (US); Maie Taha, El-Mohandeseen Giza (EG)

(73) Assignee: Brixton Biosciences, Inc., Cambridge, MA (US)

( * ) Notice: Subject to any disclaimer, the term of this patent is extended or adjusted under 35 U.S.C. 154(b) by 240 days.

(21) Appl. No.: 18/569,188

(22) PCT Filed: Jun. 10, 2022

(86) PCT No.: PCT/US2022/033095

§ 371 (c)(1),
(2) Date: Dec. 11, 2023

(87) PCT Pub. No.: WO2022/261494

PCT Pub. Date: Dec. 15, 2022

(65) Prior Publication Data

US 2024/0285529 A1 Aug. 29, 2024

Related U.S. Application Data

(60) Provisional application No. 63/209,646, filed on Jun. 11, 2021.

(51) Int. Cl.
*A61K 9/107* (2006.01)
*A61K 9/127* (2025.01)
*A61K 31/685* (2006.01)

(52) U.S. Cl.
CPC .............. *A61K 9/107* (2013.01); *A61K 9/127* (2013.01); *A61K 31/685* (2013.01)

(58) Field of Classification Search
CPC ....... A61K 9/107; A61K 9/127; A61K 31/685
See application file for complete search history.

(56) References Cited

U.S. PATENT DOCUMENTS 5,869,092 A 2/1999 Hays et al.
6,465,425 B1 10/2002 Tracy et al.
6,962,601 B2 11/2005 Becker et al.
7,344,531 B2 3/2008 Bischof et al.
7,900,452 B2 3/2011 Howard et al.
8,362,062 B2 1/2013 Tawa et al.
8,709,484 B2 4/2014 Weers et al.
8,932,610 B2 1/2015 Ruiz I Pol et al.
9,649,220 B2 5/2017 Anderson et al.
9,822,243 B2 11/2017 Malessa et al.
10,555,831 B2 2/2020 Jimenez Lozano et al.
10,682,297 B2 6/2020 Zeng et al.
11,241,330 B1 2/2022 Sabir et al.
11,504,322 B2 11/2022 Garibyan et al.
2009/0125087 A1 5/2009 Becker et al.
2011/0088413 A1 4/2011 Lampe et al.
2011/0196026 A1 8/2011 De et al.
2015/0282502 A1 10/2015 Ummadi et al.
2015/0366975 A1 12/2015 Jhan et al.
2017/0274011 A1 9/2017 Garibyan et al.
2017/0274078 A1* 9/2017 Garibyan ............. A61K 31/718
2017/0325992 A1 11/2017 DeBenedictis et al.
2017/0326042 A1* 11/2017 Zeng ...................... A61K 9/127
2017/0326346 A1 11/2017 Jimenez Lozano et al.
2019/0053939 A1 2/2019 Garibyan et al.
2019/0082715 A1 3/2019 Giuseppin et al.
2019/0183558 A1 6/2019 Anderson et al.
2019/0192424 A1* 6/2019 Garibyan ............... A61K 47/26
(Continued)

FOREIGN PATENT DOCUMENTS

CA 2563170 C 10/2011
EP 1453916 B1 5/2011
JP 2001131538 A 5/2001
(Continued)

OTHER PUBLICATIONS

Excipient to pass through a lipid bilayer—Google Search (Year: 2025).*
Liposome—Google Search (Year: 2025).*
Propylene glycol liposomes—Google Search (Year: 2025).*
Bodratti, A.M. and Alexandridis, P., "Formulation of Poloxamers for Drug Delivery," Journal of Functional Biomaterials, vol. 9, No. 11, pp. 1-24, doi:10.3390/jfb9010011 (Published Jan. 18, 2018).
Cleary, C., et al., "Advanced fluids for district cooling systems; A review and progress report," Copenhagen Denmark, Research Organizations: Nordisk Ministerraad; Danmarks Tekniske Hoejskole, Lyngby (Denmark). Lab. for Varme-og Klimateknik, Report No. CONF-9104191-, Reference No. DK-91-001576; EDB-91-140140, Jan. 1, 1991, 3 total pages (Abstract Only).
(Continued)

*Primary Examiner* — Robert A Wax
*Assistant Examiner* — John W Lippert, III
(74) *Attorney, Agent, or Firm* — Wilmer Cutler Pickering Hale and Dorr LLP

(57) ABSTRACT

Disclosed herein is a composition comprising: an amount of water; a non-water-soluble substance; and a first excipient, wherein the composition is configured to form a flowable ice slurry when exposed to freezing temperatures. Also disclosed herein is a method of preparing a cold slurry for administration to a patient at a clinical point of care, the method comprising: preparing a composition comprising a plurality of lipid particles; adding an excipient to the composition, wherein the excipient is configured to reduce the freezing point of a volume external to the plurality of lipid particles and of a volume internal to the plurality of lipid particles; and cooling the composition to a predetermined temperature such that the cold slurry is formed, wherein the cold slurry comprises a plurality of ice particles.

15 Claims, 4 Drawing Sheets

(56) References Cited

U.S. PATENT DOCUMENTS

| | | | |
|---|---|---|---|
| 2021/0106383 | A1 | 4/2021 | Alas et al. |
| 2022/0079648 | A1 | 3/2022 | Stefater, III et al. |

FOREIGN PATENT DOCUMENTS

| | | | | |
|---|---|---|---|---|
| JP | 2008518951 | A | 6/2008 | |
| JP | 2017-529336 | A | 10/2017 | |
| WO | WO-9617899 | A1 * | 6/1996 | ........... C11B 5/0071 |
| WO | WO-2001/08464 | A2 | 2/2001 | |
| WO | WO-2016/033380 | A1 | 3/2016 | |
| WO | WO-2017/147367 | A1 | 8/2017 | |
| WO | WO-2017/196548 | A1 | 11/2017 | |
| WO | WO-2021/016457 | A1 | 1/2021 | |
| WO | WO-2021/195582 | A1 | 9/2021 | |
| WO | WO-2022/055934 | A1 | 3/2022 | |
| WO | WO-2022/211904 | A1 | 10/2022 | |
| WO | WO-2022/261494 | A1 | 12/2022 | |
| WO | WO-2023/154902 | A1 | 8/2023 | |

OTHER PUBLICATIONS

Emmanuel, A., E., O., "Molecular Simulation of Ice Growth Inhibition by Biomimetic Antifreeze Macromolecules," Thesis Submitted for the Degree of PhD at the University of Warwick, http://wrap.warwick.ac.uk/81957, Dec. 2015, 262 total pages.

International Preliminary Report on Patentability issued Aug. 22, 2024 by U.S. Patent and Trademark Office as Searching Authority for International Bureau of WIPO in International Patent Application No. PCT/US23/62443 (11 total pages).

International Preliminary Report on Patentability issued Dec. 21, 2023 by U.S. Patent and Trademark Office as International Searching Authority for International Bureau of WIPO in International Patent Application No. PCT/US22/33095 (8 total pages).

International Search Report and the Written Opinion issued Jul. 3, 2023 by U.S. Patent and Trademark Office as Searching Authority for International Bureau of WIPO in International Patent Application No. PCT/US23/62443 (22 total pages).

International Search Report and Written Opinion issued Oct. 26, 2022 by U.S. Patent and Trademark Office as International Searching Authority for International Bureau of WIPO in International Patent Application No. PCT/US22/33095 (16 total pages).

Invitation to Pay Additional Fees and, Where Applicable, Protest Fee issued Apr. 27, 2023 by U.S. Patent and Trademark Office as Searching Authority for International Bureau of WIPO in International Patent Application No. PCT/US23/62443 (3 total pages).

Invitation to Pay Additional Fees and, Where Applicable, Protest Fee issued Aug. 30, 2022 by U.S. Patent and Trademark Office as International Searching Authority for International Bureau of WIPO in International Patent Application No. PCT/US22/33095 (2 total pages).

Kitamoto, D., "Functions and potential applications of glycolipid biosurfactants—from energy—saving materials to gene delivery carriers," Journal of Bioscience and Bioengineering, vol. 94, Issue 3, pp. 187-201, Sep. 2002 (Abstract Only, 2 total pages).

Kitamoto, D., "Production of Glycolipid Biosurfactants and Their Functional Development," vol. 3., No. 12, 663-672 (11 total pages) with English abstract (Year: 2003).

Kitamoto, D., et al., "Remarkable Antiagglomeration Effect of a Yeast Biosurfactant, Diacylmannosylerythritol, on Ice-Water Slurry for Cold Thermal Storage," Biotechnology Progress, vol. 17, Issue 2, https://doi.org/10.1021/bp000159f (first published Sep. 5, 2008)—English Abstract Only retrieved from https://aiche.onlinelibrary.wiley.com/doi/abs/10.1021/bp000159f (6 total pages).

Kozloff, L.M., et al., "Phosphatidylinositol, a Phospholipid of Ice-Nucleating Bacteria," Journal Of Bacteriology, vol. 173, No. 6, pp. 2053-2060 (Mar. 1991).

Lu, S.-S., et al., "Microscale study of poly(vinyl alcohol) as an effective additive for inhibiting recrystallization in ice slurries," International Journal of Refrigeration, vol. 25, Issue 5, pp. 562-568, Aug. 2002—English Abstract Only retrieved from https://www.sciencedirect.com/science/article/abs/pii/S0140700701000457 (3 total pages).

Matsumoto, K., et al., "Investigation of the influence of surfactant on the degree of supercooling (coexisting system of solid-liquid and gas-liquid interfaces)," International Journal of Refrigeration, vol. 36, Issue 4, pp. 1302-1309, Jun. 2013—English Abstract ONLY retrieved from https://www.sciencedirect.com/science/article/abs/pii/S0140700713000303 (3 total pages).

Modak, P. R., et al., "Agglomeration Control of Ice Particles in Ice-Water Slurry System Using Surfactant Additives," HVAC&R Research, vol. 8, No. 4, pp. 453-466 (Oct. 2002).

Modak, P. R., et al., "Effect of Cetyldimethylbetaine Molecules on Agglomeration and Growth of Ice," vol. 33, No. 12, year: 2004, https://doi.org/10.1246/cl.2004.1558, 4 total pages (Abstract Only).

No Author, "Polysorbate 80—PubChem Reference Collection SID 481110309," last retrieved on Nov. 21, 2024 from https://pubchem.ncbi.nlm.nih.gov/compound/Polysorbate-80 (38 total pages).

No Author, "Polysorbate 80—Synonyms," last retrieved on Nov. 21, 2024 from https://pubchem.ncbi.nlm.nih.gov/compound/Polysorbate-80#section=Synonyms&fullscreen=true (6 total pages).

No Author, "Tween 20—PubChem CID 443314," last retrieved on Nov. 21, 2024 from https://pubchem.ncbi.nlm.nih.gov/compound/443314 (37 total pages).

Oignet, J., et al., "Rheological study of CO 2 hydrate slurry in the presence of Sodium Dodecyl Sulfate in a secondary refrigeration loop," Chemical Engineering Science, vol. 158, pp. 294-303, ISSN 0009-2509 https://doi.org/10.1016/j.ces.2016.10.018, (Year: 2017) 12 total pages.

Raju, R., et al., "Interactions of cryoprotective agents with phospholipid membranes—a Langmuir monolayer study," Chemistry and Physics of Lipids, Chemistry and Physics of Lipids, Journal Pre-proof, Accepted Jul. 14, 2020 (19 total pages), doi: https://doi.org/10.1016/j.chemphyslip.2020.104949.

Rinaldi, M., et al., "Innovation in the Italian ice cream production: effect of different phospholipid emulsifiers," Dairy Science & Technology, vol. 94, No. 1, pp. 33-49, EDP sciences/Springer, Sep. 2014, DOI: 10.1007/s13594-013-0146-1 (19 total pages).

Saito, A., et al., "Study on Fundamental Characteristics of Ice Slurry of Propylene Glycol Solution," Trans. of the JSRAE, vol. 22, No. 1, pp. 55-62 with English summary (Year: 2005).

Suzuki, H., et al., "Particle Size Depression and Drag Reduction of Ice Slurry Treated with Combination Additives of Surfactants and Poly(vinyl alcohol)," Journal of Chemical Engineering of Japan, vol. 43, No. 6, pp. 482-486, https://doi.org/10.1252/jcej.43.482 (Year: 2010).

Suzuki, H., et al., "Particle Size Characteristics of Ice Slurry Treated with Surfactants and Brines," Journal of Chemical Engineering of Japan, 42, No. 6, p. 447-451 (Accepted on Mar. 30, 2009).

Suzuki, H., et al., "Vacuum Production Characteristics of Ice Slurries Treated with Surfactants," Trans. of the JSRAE, vol. 25, No. 2 pp. 177-184 with English summary (Year: 2008).

Usui, H., et al., "Suppression of Ice Particle Growth and the Possibility of Energy Saving Latent Heat Transportation by Using Surfactant Additives," Journal of Chemical Engineering of Japan, vol. 37, Issue 1, pp. 15-22, https://doi.org/10.1252/jcej.37.15 (Year: 2004)—English Abstract Only retrieved from https://www.jstage.jst.go.jp/article/jcej/37/1/37_1_15/_article/-char/ja/ (3 total pages).

Extended European Seach Report issued Mar. 14, 2025 by European Patent Office in European Patent Application No. 22821155.3 (11 total pages).

Extended European Search Report issued Feb. 26, 2026 by European Patent Office in European Patent Application No. 23753729.5 (23 total pages).

Notice of Grounds for Rejection issued Mar. 18, 2026 by Japanese Patent Office in Japanese Patent Application No. 2023-576327 with English translation (13 total pages).

* cited by examiner

METHODS OF CREATING A SLURRY USING LIPOSOME EMULSIONS

CROSS-REFERENCE TO RELATED APPLICATIONS

This application is a U.S. National Stage application under 35 U.S.C. § 371 of International Patent Application No. PCT/US2022/033095, filed on Jun. 10, 2022, which claims priority under 35 U.S.C. § 119 (e) to U.S. Ser. No. 63/209,646, filed Jun. 11, 2021, the contents of each of which are hereby incorporated by reference in their entireties.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

INCORPORATION BY REFERENCE

The contents of each of the following are hereby incorporated by reference in their entireties: U.S. Publication No. US2017/0274011 ("'011 Publication"; U.S. application Ser. No. 15/505,042); U.S. Publication No. US2017/0274078 ("'078 Publication"; U.S. application Ser. No. 15/505,039); U.S. Publication No. US2019/0053939 ("'939 Publication"; U.S. application Ser. No. 15/505,039); and International Publication No. WO2021/016457.

TECHNICAL FIELD

The present disclosure relates generally to compositions and methods for manufacturing biomaterials that form flowable and/or injectable cold slurries.

BACKGROUND

Cold slurries (e.g., ice slurries) are known in the art as compositions that are made of sterile ice particles of water, varying amounts of excipients or additives such as freezing point depressants, hydrotropic molecules, and, optionally, one or more active pharmaceutical ingredients, as described in the '011 Publication, incorporated by reference in its entirety herein. Prior art cold slurries can be delivered, preferably via injection, to a tissue of a subject, preferably a human patient, to cause selective or non-selective cryotherapy and/or cryolipolysis for prophylactic, therapeutic, or aesthetic purposes. Injectable cold slurries may be used for treatment of various disorders that require inhibition of nerve conduction. For example, the '078 Publication, incorporated by reference in its entirety herein, discloses the use of slurries to induce reversible degeneration of nerves (e.g., through Wallerian degeneration) by causing crystallization of lipids in the myelin sheath of nerves. The '078 Publication also discloses using injectable cold slurries to treat various other disorders that require inhibition of somatic or autonomic nerves, including motor spasms, hypertension, hyperhidrosis, and urinary incontinence.

A method of preparing a cold slurry using a cold slurry production system including an actuator, cooling device, and pump (among other components) is disclosed in the '939 Publication, incorporated by reference in its entirety herein. However, the method disclosed in the '939 Publication requires the point of care to manufacture the cold slurry by installing a large, complex, and expensive medical ice slurry production system. This technique also requires the point of care to take steps to maintain sterility of the cold slurry during manufacture and prior to administration.

There exists a need for compositions and methods that allow for simple transport, storage, and preparation of a flowable and/or injectable cold slurry at a clinical point of care without compromising the sterility of the biomaterial (e.g., the solution that will be transformed into the cold slurry) during preparation, without requiring specialized manufacturing equipment to be available at the point of care, and without compromising the sterility of the biomaterial at the point of care. The present disclosure addresses this need by providing for improved cold slurry compositions and methods of preparation that allow for a biocompatible solution to be received at a point of care in an easily shipped and stored container that the point of care can place into, for example, a standard freezer to transform the biocompatible solution into a therapeutic substance, e.g., a flowable and/or injectable cold slurry.

SUMMARY

In one aspect, the present disclosure provides for a composition comprising: an amount of water; a non-water-soluble substance; and a first excipient, wherein the composition is configured to form a flowable ice slurry when exposed to freezing temperatures.

In some embodiments, the non-water-soluble substance is a lipid.

In some embodiments, the composition comprises a plurality of lipids.

In some embodiments, the composition comprises a lipid particle, and wherein the lipid particle comprises the plurality of lipids.

In some embodiments, the first excipient is configured to pass through a lipid bilayer of the lipid particle.

In some embodiments, a first solution encapsulated within the lipid particle and a second solution outside of the lipid particle are substantially equal in composition.

In some embodiments, the lipid particle is a liposome or a micelle.

In some embodiments, the lipid is a phospholipid.

In some embodiments, the phospholipid is selected from the group consisting of 1,2-distearoyl-sn-glycero-3-phosphocholine (DSPC), egg sphingomyelin (DPSM), dipalmitoylphosphatidyl (DPPC), dicethylphosphate (DCP), L-α-phosphatidylcholine (soy PC), phosphatidylethanolamine (PE), phosphatidylserine (PS), phosphatidylglycerol (PG), and a combination thereof.

In some embodiments, the phospholipid is soy PC, and wherein a concentration of the soy PC in the composition is between about 0.1 g/mL and 0.3 g/mL.

In some embodiments, the concentration of the soy PC in the composition is about 0.26 g/mL.

In some embodiments, the first excipient is selected from the group consisting of a salt, an ion, Lactated Ringer's solution, a sugar, a biocompatible surfactant, a polyol, and a combination thereof.

In some embodiments, the first excipient is glycerol.

In some embodiments, a concentration of the glycerol in the composition is between about 10% and 20% weight by volume.

In some embodiments, the concentration of the glycerol in the composition is about 15% weight by volume.

In some embodiments, the composition further comprises a second excipient.

In some embodiments, the second excipient is saline or phosphate-buffered saline (PBS).

In some embodiments, an average freezing point of a total volume of the composition is between about −25° C. and about −5° C.

In another aspect, the present disclosure provides for a method of preparing a cold slurry for administration to a patient at a clinical point of care, the method comprising: preparing a composition comprising a plurality of lipid particles; adding an excipient to the composition, wherein the excipient is configured to reduce the freezing point of a volume external to the plurality of lipid particles and of a volume internal to the plurality of lipid particles; and cooling the composition to a predetermined temperature such that the cold slurry is formed, wherein the cold slurry comprises a plurality of ice particles.

In some embodiments, the volume internal to the lipid particles is between about 20% and 50% of a total volume of the composition.

In some embodiments, a first solution comprising the volume internal to the plurality of lipid particles and a second solution comprising the volume external to the plurality of lipid particles are substantially equal in composition.

In some embodiments, the composition comprises a liposome or a micelle, and wherein the liposome or the micelle comprises the plurality of lipid particles.

In some embodiments, the plurality of lipid particles comprises a plurality of lipids, and wherein the plurality of lipids comprises a phospholipid.

In some embodiments, the phospholipid is selected from the group consisting of 1,2-distearoyl-sn-glycero-3-phosphocholine (DSPC), egg sphingomyelin (DPSM), dipalmitoylphosphatidyl (DPPC), dicethylphosphate (DCP), L-α-phosphatidylcholine (soy PC), phosphatidylethanolamine (PE), phosphatidylserine (PS), phosphatidylglycerol (PG), and a combination thereof.

In some embodiments, the phospholipid is L-α-phosphatidylcholine (soy PC), and wherein a concentration of the soy PC in the composition is between about 0.1 g/mL and 0.3 g/mL.

In some embodiments, the excipient is selected from the group consisting of a salt, an ion, Lactated Ringer's solution, a sugar, a biocompatible surfactant, a polyol, and a combination thereof.

BRIEF DESCRIPTION OF THE DRAWINGS

The following figures depict illustrative embodiments of the present disclosure.

DEFINITIONS

Figure 1:
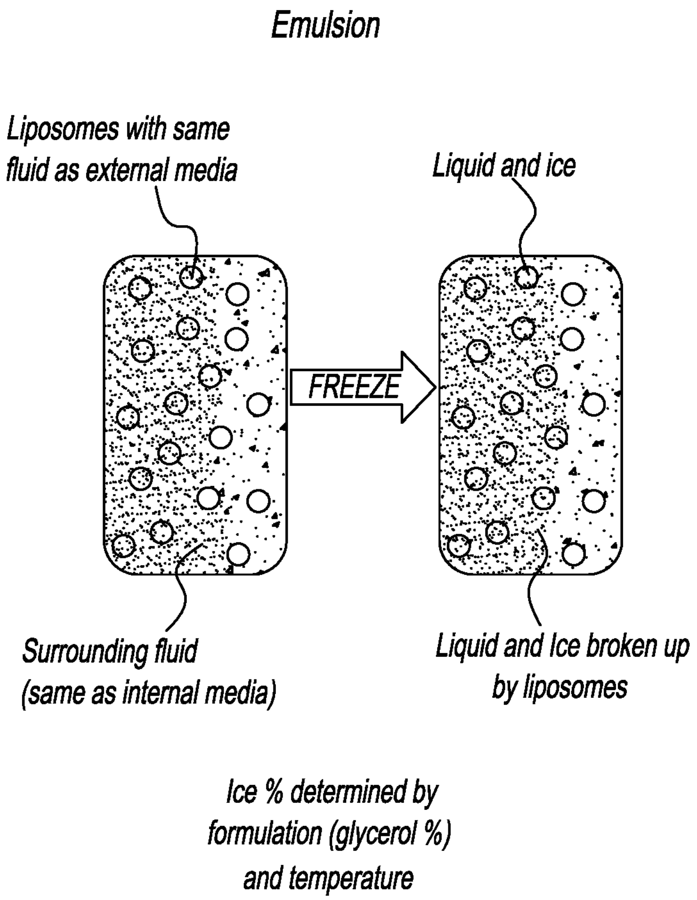
FIG. 1 depicts an embodiment of a liposome emulsion composition.

The following are definitions of terms used in the present specification. The initial definition provided for a group or term herein applies to that group or term throughout the present specification individually or as part of another group, unless otherwise indicated. Unless otherwise defined, all technical and scientific terms used herein have the same meaning as commonly understood by one of ordinary skill in the art.

As used herein, the term "excipient" means any substance, not itself a therapeutic agent, used as a diluent, adjuvant, and/or vehicle for delivery of a therapeutic agent (in this case the therapeutic agent is the ice) to a subject or patient, and/or a substance added to a composition to improve its handling, stability, or storage properties. The terms "excipient" and "additive" are used interchangeably herein.

DETAILED DESCRIPTION

The present disclosure relates generally to compositions and methods for manufacturing biomaterials that form flowable and/or injectable cold slurries. In some embodiments, the composition contains lipids, lipid particles (e.g., liposomes) or other lipid structures (e.g., lamellar or non-lamellar structures, bilayer and non-bilayer structures, including lipid nanoparticles, micelles, etc.), or non-water-soluble substances (i.e., substances that do not dissolve in water. In some embodiments, the composition forms an emulsion.

The present disclosure describes compositions that, when frozen, result in flowable and/or injectable cold slurries. In some embodiments, the compositions of the present disclosure do not require mixing or manipulation to be flowable and/or injectable, however, manipulation may be used in other embodiments to further improve flowability and/or injectability or to promote consistency. In some embodiments, the compositions comprise a suspension of fluid with high water content (e.g., between about 70% v/v and 80% v/v, between about 80% v/v and 90% v/v, or greater than about 90% v/v), a solute used to depress the freezing point (e.g., glycerol), and/or a lipid (or a different non-water-soluble compound).

In some embodiments, the composition is an emulsion which contains an effective amount of a lipid (or a different non-water-soluble compound) to create a flowable and/or injectable cold slurry. In some embodiments, compositions described herein are transformed into flowable and/or injectable cold slurries having ice particles when placed into a standard freezer (or any other cold environment) without requiring the application of any mechanical agitation or additional treatment.

In some embodiments, an emulsion is any composition described herein that comprises a lipid (or a different non-water-soluble compound). In some embodiments, a plurality of lipids in the composition are assembled into lipid particles having one or more morphologies (e.g., lamellar or non-lamellar structures, bilayer and non-bilayer structures, including liposomes, lipid nanoparticles, micelles, etc.). The lipid particle morphology of the present disclosure may be determined by any method known in the art such as by CryoTEM. In some embodiments, the lipid particles in the composition are between about 5 μm and about 300 μm in diameter. In some embodiments, the lipid particles are about 250 μm in diameter. In some embodiments, the lipid particles in the composition are between about 5 μm and 20 μm in diameter, or between about 8 μm and 14 μm in diameter. Without intending to be bound by any particular theory, it is believed that the lipid(s) or non-water-soluble compound(s) prevent ice particles from growing too large when the composition is exposed to freezing temperatures such that the composition is no longer flowable and/or injectable.

In some embodiments, one or more excipients may be included in the cold slurry. As used herein, the term "excipient" means any substance, not itself a therapeutic agent, used as a diluent, adjuvant, and/or vehicle for delivery of a therapeutic agent (in this case the therapeutic agent is the ice) to a subject or patient, and/or a substance added to a composition to improve its handling, stability, or storage properties (e.g., an additive). Excipients can constitute less than about 10% volume by volume (v/v), between about 10% v/v and about 20% v/v, between about 20% v/v and about 30% v/v, between about 30% v/v and 40% v/v, and greater than about 40% v/v of the cold slurry. Various added excipients can be used to alter the phase change temperature of the cold slurry (e.g., reduce the freezing point), alter the ice percentage of the cold slurry, alter the viscosity of the cold slurry, prevent agglomeration of the ice particles, prevent dendritic ice formation (i.e., crystals with multi-branching "tree-like" formations, such as those seen in snowflakes), keep ice particles separated, increase thermal conductivity of fluid phase, or improve the overall prophylactic, therapeutic, or aesthetic efficacy of the flowable and/or injectable cold slurry. In the compositions described herein, such excipients may include non-water-soluble substances or lipids (including lipid particles), which can prevent agglomeration of the ice particles, prevent dendritic ice formation (i.e., crystals with multi-branching "tree-like" formations, such as those seen in snowflakes), or keep ice particles separated, such that the cold slurry is flowable and/or injectable when it is removed from a cold environment (e.g., a freezer).

In some embodiments, a first excipient is selected from the group consisting of a salt, an ion, Lactated Ringer's solution, a sugar, a biocompatible surfactant, a polyol, and a combination thereof. In some embodiments, the excipient is a polyol. In some embodiments, the polyol is glycerol.

In some embodiments, the composition further includes a second excipient. In some embodiments, the second excipient is saline or phosphate-buffered saline (PBS).

In some embodiments, the first, second, or any additional excipient suitable for compositions described herein include sucrose, lactose, trehalose, mannitol, sorbitol, glucose, raffinose, glycine, histidine, PVP (K40), sodium citrate, sodium phosphate, sodium hydroxide, tris base-65, tris acetate, tris HCl-65, dextrose, dextran, ficoll, gelatin, hydroxyethyl starch, Benzalkonium chloride, benzethonium chloride, benzyl alcohol, chlorobutanol, m-cresol, myristyl gamma-picolinium chloride, paraben methyl, paraben propyl, phenol, 2-penoxyethanol, phenyl mercuric nitrate, thimerosal, calcium disodium EDTA (ethylenediaminetetra acetic acid), disodium EDTA, calcium versetamide sodium, calteridol, DTPA, acetone sodium bisulfate, argon, ascorbyl palmitate, ascorbate (sodium/acid), bisulfite sodium, butylated hydroxyl anisole, butylated hydroxyl toluene (BHT), cystein/cysteinate HCl, dithionite sodium, gentistic acid, gentistic acid ethanolamine, glutamate monosodium, glutathione, formaldehyde sulfoxylate sodium, metabisulfite potassium, metabisulfite sodium, methionine, monothioglycerol (thioglycerol), nitrogen, propyl gallate, sulfite sodium, tocopherol alpha, alpha tocopherol hydrogen succinate, thioglycolate sodium, thiourea, anhydrous stannous chloride, Benzyl benzoate, castor oil, cottonseed oil, N,N dimethylacetamide, ethanol, dehydrated ethanol, glycerin/glycerol, N-methyl-2-pyrrolidone, peanut oil, PEG, PEG 300, PEG 400, PEG 600, PEG 3350, PEG 1000, PEG 4000, poppyseed oil, propylene glycol, safflower oil, sesame oil, soybean oil, vegetable oil, oleic acid, polyoxyethylene castor, sodium acetate-anhydrous, sodium carbonate anhydrous, triethanolamine, deoxycholate acetate, ammonium sulfate, ammonium hydroxide, arginine, aspartic acid, benzenesulfonic acid, benzoate sodium/acid, bicarbonate-sodium, boric acid/sodium, carbonate/sodium, carbon dioxide, citrate, diethanolamine, glucono-delta-lactone, glycine/glycine HCl, histidine/histidine HCl, hydrochloric acid, hydrobromic acid, L-lysine, maleic acid, meglumine, methanesulfonic acid, monoethanolamine, phosphate (acid, monobasic potassium, dibasic potassium, monobasic sodium, dibasic sodium and tribasic sodium), sodium hydroxide, succinate sodium/disodium, sulfuric acid, tartarate sodium/acid, tromethamine (Tris), aminoethyl sulfonic acid, asepsis sodium bicarbonate, L-cysteine, dietholamine, diethylenetriaminepentacetic acid, fenic chloride, albumin, hydrolyzed gelatin, insitol, D,L-methionine, Polyoxyethylene sorbitan monooleate (TWEEN® 80), sorbitan monooleate, polyoxyethylene sorbitan monolaurate (TWEEN® 20), lecithin, polyoxyethylene polyoxypropylene copolymers (PLURONICS®), polyoxyethylene monolaurate, phosphatidylcholine, glyceryl fatty acid esters, urea, Cyclodextrins (e.g., hydroxypropyl-β-cyclodextrin, sulfobutylether-β-cyclodextrin), sodium carboxymethyl cellulose, acacia, gelatin, methyl cellulose, and polyvinyl pyrrolidone.

In some embodiments, the composition includes a lipid particle. In some embodiments, the lipid particle is a liposome. In some embodiments, the lipid particle is a micelle. In some embodiments, the lipid particle is a phospholipid. In some embodiments, the phospholipid is selected from the group consisting of 1,2-distearoyl-sn-glycero-3-phosphocholine (DSPC), egg sphingomyelin (DPSM), dipalmitoylphosphatidylcholine (DPPC), dicethylphosphate (DCP), L-α-phosphatidylcholine (PC), phosphatidylethanolamine (PE), phosphatidylserine (PS), phosphatidylglycerol (PG), and a combination thereof. In some embodiments, the lipid is soy PC.

One or more freezing point depressants can be added as an excipient to sterile water to form a cold slurry with a freezing point below 0° C. (e.g., about −10° C.). Depressing the freezing point of the cold slurry allows it to maintain flowability and/or remain injectable while still containing an effective percentage of ice particles. Suitable freezing point depressants include salts (e.g., sodium chloride, betadex sulfobutyl ether sodium), ions, Lactated Ringer's solution, sugars (e.g., glucose, sorbitol, mannitol, hetastarch, sucrose, (2-Hydroxypropyl)-β-cyclodextrin, or a combination thereof), biocompatible surfactants such as glycerol (also known as glycerin or glycerine), other polyols (e.g., polyvinyl alcohol, polyethylene glycol 300, polyethylene glycol 400, propylene glycol), other sugar alcohols, or urea, and the like. Other exemplary freezing point depressants are disclosed in the '011 Publication, incorporated in its entirety herein.

In some embodiments, the composition further includes ethanol. In some embodiments, the concentration of ethanol in the composition is between about 0.01% v/v and 0.1% v/v. In some embodiments, the concentration of ethanol in the composition is about 0.07% v/v or less.

In some embodiments, the composition is filled into a container with a volume less than 10 mL and with a shape that results in maximum surface area. Without intending to be bound by any particular theory, it is believed that the large surface area-to-volume ratio facilitates an increased freezing rate to further prevent large ice crystal formation and therefore improve flowability and/or injectability of the cold slurry. In some embodiments, a total injection volume of the cold slurry into a patient is between about 40 mL and 50 mL, between about 50 mL and 60 mL, between about 60 mL and 70 mL, or more than about 70 mL. In some embodiments, the total injection volume is about 60 mL.

A method of creating a cold slurry by formulating a solution that prevents the formation of large ice crystals by separating the internal and external volume across liposomal membranes is described in International Publication No. WO2021/016457, incorporated by reference in its entirety herein. In some embodiments, described herein is an unexpected method of forming a cold slurry by creating a composition having a lipid, water, and at least one excipient, without separating the internal and external media across a liposomal membrane. In other words, the material surrounding a liposomal membrane is the same as the material encapsulated within the liposomal membrane. In some embodiments, there is no liposome formed, and lipids are dispersed in the composition. Another advantage of the current compositions is the ability to create a cold slurry that does not require any mechanical manipulation or agitation of the composition.

In some embodiments, the composition described herein is a homogenous mixture such that the composition media throughout the container is uniform and the components are distributed evenly. In some embodiments, the addition of a non-water soluble substance prevents the formation of large ice crystals such that a flowable cold slurry can be injected into a subject or applied topically immediately after removal of the cold slurry from the freezer or another cold environment.

Referring to FIG. 1, an embodiment of a liposome emulsion composition is shown. In this embodiment, the media inside and outside the liposomes is substantially the same. In some embodiments, the liposome emulsion composition includes an excipient and/or a freezing point depressant (e.g., glycerol). Glycerol is relatively small and will penetrate the liposome membrane such that it is free-flowing inside and outside the formed liposomes. In some embodiments, the selected excipient is able to cross the liposome barrier such that the media inside the liposome is homogenous with the media outside the liposome. In some embodiments, the liposomes in the composition are between about 5 μm and about 300 μm in diameter. In some embodiments, the liposomes are about 250 μm in diameter. In some embodiments, the liposomes are between about 5 μm and 20 μm in diameter, or between about 8 μm and 14 μm in diameter. In some embodiments, the liposomes are about 10 μm in diameter. In some embodiments, the liposomes vary in size throughout the composition and can have a random distribution (e.g., a normal distribution) of size such that the composition can include a larger number of liposomes per unit volume. In some embodiments, the liposomes are not closed structures that encapsulate a media and instead lipids or other non-water soluble substances are dispersed throughout the composition.

In some embodiments, the encapsulated volume of the liposomes in the emulsion composition is between about 20% and about 50% of a total volume of the composition. In some embodiments, the encapsulated volume is between about 30% and about 40% of a total volume of the composition. In some embodiments, the encapsulated volume is between about 40% and about 50% of a total volume of the composition. In some embodiments, the encapsulated volume is between about 35% and about 40% of a total volume of the composition. In some embodiments, the encapsulated volume is between about 40% and about 45% of a total volume of the composition. In some embodiments, the encapsulated first volume is about 38% of the total volume of the composition. In some embodiments, the encapsulated first volume is about 43% of the total volume of the composition. In some embodiments, the encapsulated volume affects the flowability and injectability of the cold slurry.

Figure 2:
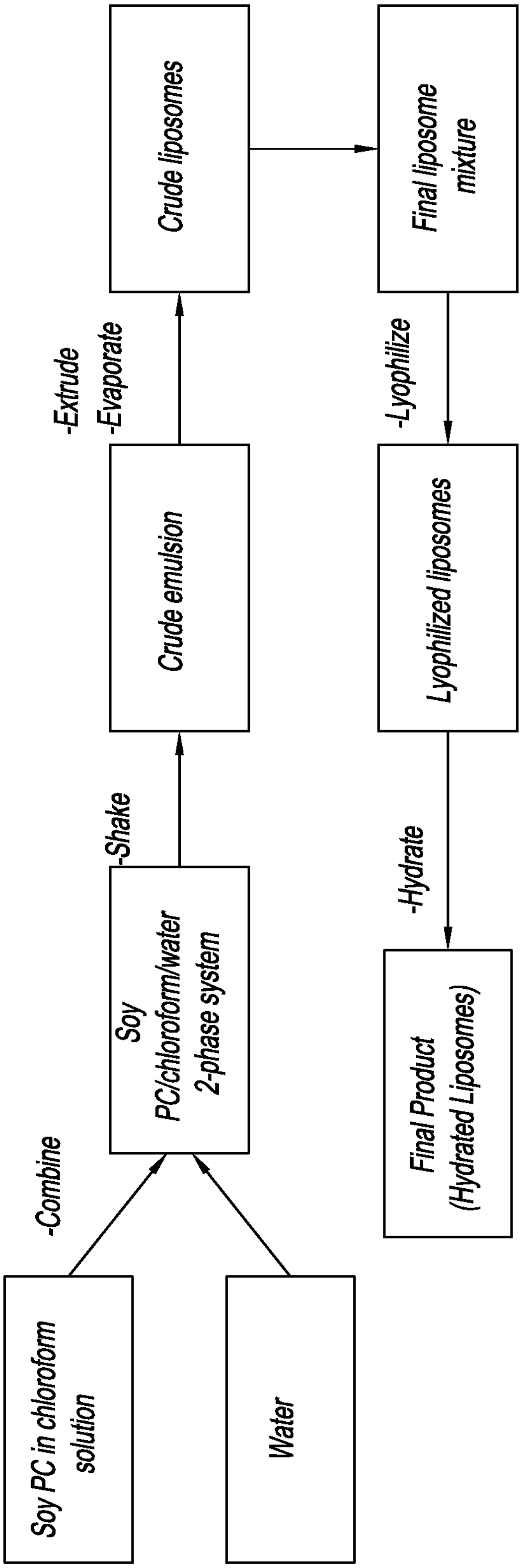
FIG. 2 depicts a process flow diagram for creating a liposome emulsion composition.

FIG. 2 shows a process flow diagram for creating lipid particle (e.g., liposome) emulsions compositions in accordance with some embodiments of the present disclosure. As shown in the embodiment depicted in FIG. 2, the process begins by combining a phospholipid (e.g., soy PC) in chloroform solution with water to create a two-phase system. This two-phase system is then agitated (e.g., by shaking) to create a crude emulsion composition. The crude emulsion composition is subjected to extrusion and/or evaporation steps to create a crude liposome composition and then a final liposome mixture. In some embodiments, the crude mixture may be homogenized to create the final mixture that is more uniform and easier to process than the crude mixture. The final liposome mixture is then lyophilized to create a lyophilized liposome composition. The lyophilized liposome composition can then be hydrated to create the final hydrated liposome composition product. The process as shown in FIG. 2 is described in greater detailed herein in Example 1. Although the embodiment of FIG. 2 refers to a liposomal composition, the method may also be used to create other lipid particles known in the art with different morphologies (e.g., lamellar or non-lamellar structures, bilayer and non-bilayer structures, including lipid nanoparticles, micelles, etc.).

Figure 3:
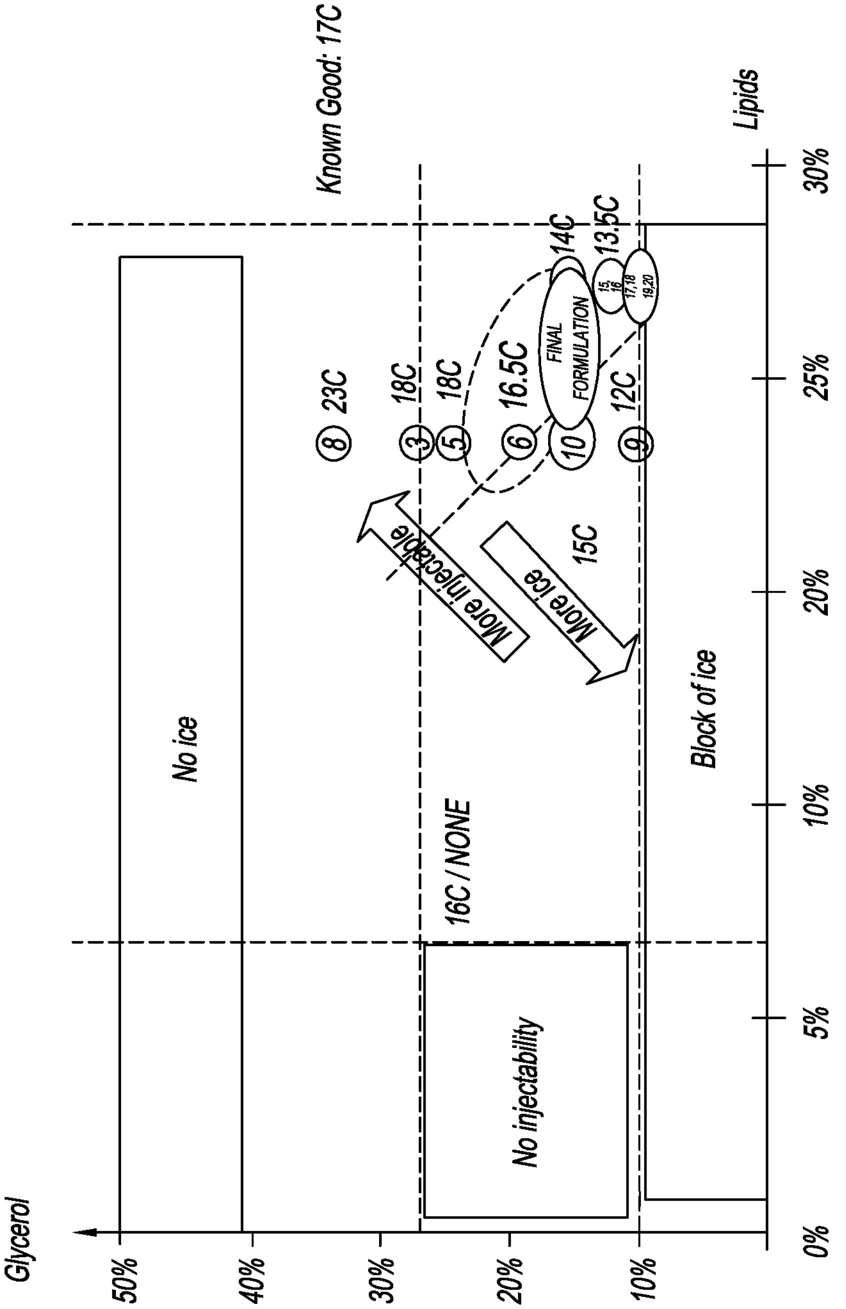
FIG. 3 is a graph showing cold slurry characterization across differing levels of excipient (glycerol) and lipids.

It has been surprisingly found that the percentage of each component of the composition can influence functionality of some embodiments of the composition. FIG. 3 shows cold slurry characterization across differing levels of excipient (glycerol) and lipids. FIG. 3 shows that higher lipid content results in increased flowability and injectability and that higher content of glycerol/excipient results in less ice percentage at a given temperature. This demonstrates that the excipient affects the freezing point. FIG. 3 shows that the lower the equilibrium temperature, the more ice percentage in the given cold slurry.

In certain embodiments, the composition is a mixture that is stable in its suspended form, or an emulsion, consisting of water, glycerol, and saline (or PBS), and lipids and contains sufficient ice particles to be flowable and/or injectable without the addition of other excipients. It has also been discovered that increasing the rate of freezing of the material further improves flowability and/or injectability of the composition. Optimization of the freezing rate includes selecting a material for the container, the geometry of the container, and the selection of the cold environment or freezer (e.g., the humidity of the freezer may be modulated to improve the flowability and/or injectability of the resulting cold slurry).

In some embodiments, the composition includes a lipid. In some embodiments, the composition includes a plurality of lipids in the form of a liposome formed from phospholipids (e.g., soy PC). The lipid may be of any type (e.g., phospholipid, cholesterol, conjugated lipid, or a combination thereof) or the composition may include any other non-water-soluble substance instead of a lipid. The lipid (or lipid particle), or non-water-soluble substance, is present in a concentration preferably between about 6% w/v and 28% w/v of the composition. Without intending to be bound by any particular theory, it is believed that the lipids (or lipid particles such as liposomes) or non-water-soluble substances create an emulsion, and when the composition is exposed to freezing temperatures (e.g., between about −25° C. and −15° C., between about −15° C. and −10° C., between about −15°

C. and −5° C., between about −10° C. and −5° C., or in some embodiments about −10° C.) because these substances prevent large crystalline formations of ice. This allows the composition to have ice particles while also being flowable and/or injectable.

In some embodiments, the composition is stable in its suspended form, or becomes an emulsion when lipids are added. In some embodiments, the composition consists of water, a freezing point depressant (e.g., glycerol), an excipient, and a non-water soluble substance. In some embodiments, the non-water soluble substance prevents large ice crystal growth.

Figure 4:
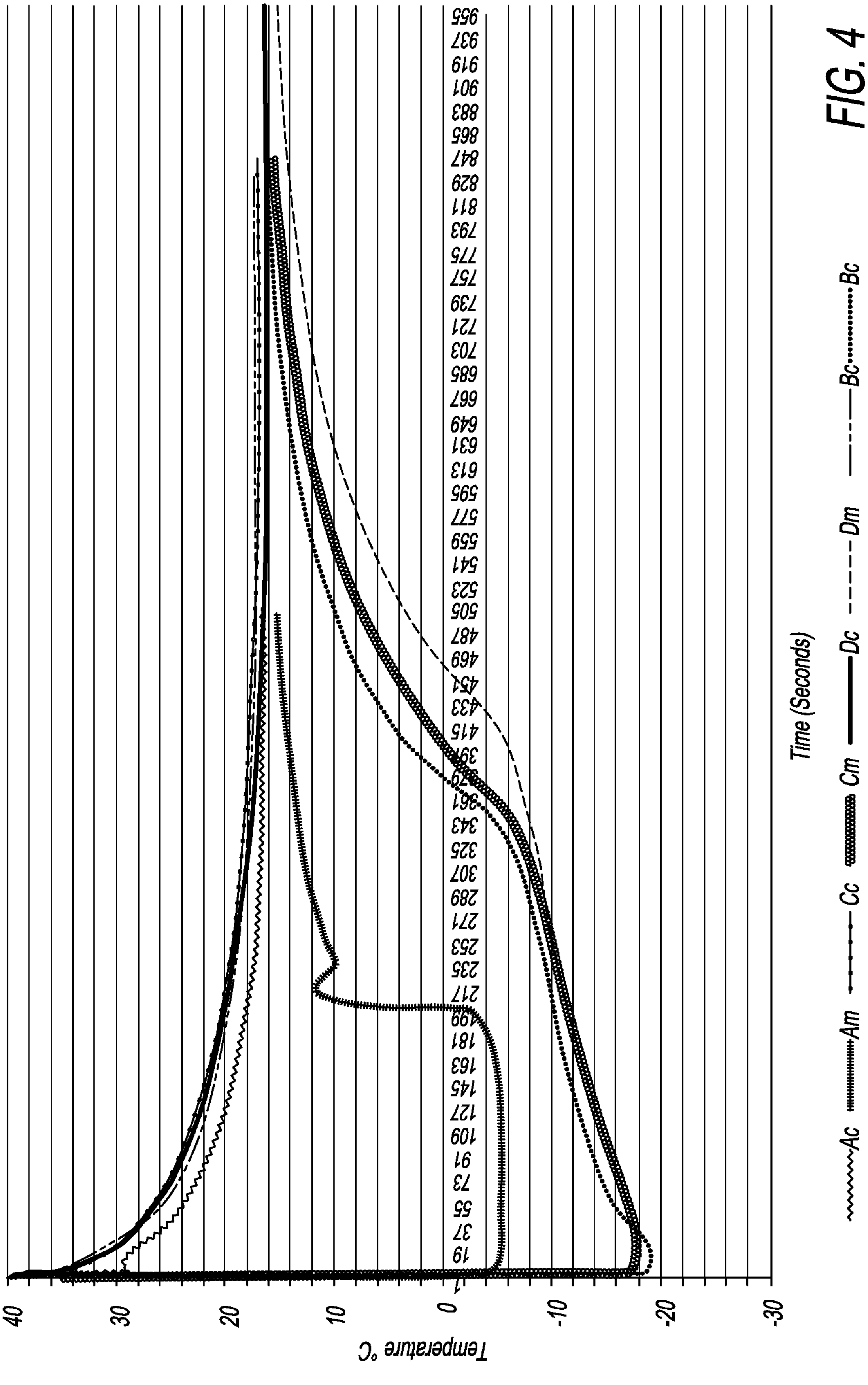
FIG. 4 is a graph showing the characterization of ice content of cold slurry control and emulsion compositions.

Referring to FIG. 4, different cold slurry compositions (batches) are characterized with respect to their temperature profiles and ice content. The different cold slurry batches were placed into a copper plate that is heated to 40° C. and has thermocouple wires that measure changes in temperature of the cold slurry over time. The plotted data shows temperature change over time for three different cold slurry batches. The temperatures are measured at two different positions for each cold slurry: embedded inside of the copper plate (traces $A_c$, $B_c$, $C_c$, and $D_c$) and in the middle of the copper plate exposed to the outside of the plate (traces $A_m$, $B_m$, $C_m$, and $D_m$). The temperature traces show three separately created cold slurry batches: a cold slurry composition having glycerin and a depressed freezing setpoint of −3.4° C. is represented by traces $A_c$ and $A_m$ (i.e., a control composition without a lipid). Three different cold slurry batches having 15% weight/volume glycerin, 0.26 grams/mL of soy PC, and PBS are represented by traces $B_c$ and $B_m$, $C_c$ and $C_m$, $D_c$ and $D_m$. In some embodiments, the cold slurry batches shown in FIG. 4 can be manufactured using the methods described in Example 1 herein. When a cold slurry batch is first introduced into the copper plate, the thermocouple wire embedded inside the plate (traces $A_c$, $B_c$, $C_c$, and $D_c$) initially measures the warm temperature of the heated plate (e.g., 31° C. for trace $A_c$ at timepoint 0) then reaches an equilibrium at a lower temperature due to the cooling effect of the introduced cold slurry (e.g., 22° C. for trace $A_c$ at around 2 minutes). On the other hand, for the thermocouple wire located in the middle of the plate, when a cold slurry is first introduced into the copper plate it immediately contacts the thermocouple wire since that wire is exposed. This causes an initially negative temperature reading in the middle position due to the crystallized cold slurry contacting the wire (e.g., −4° C. for trace $A_m$ at timepoint 0) followed by an equilibrium at a warmer temperature as the cold slurry begins to melt on the heated plate (e.g., 18° C. for trace $A_m$ at around 4 minutes). The thermocouple wire exposed to the outside of the plate (traces $A_m$, $B_m$, $C_m$, and $D_m$) can be used to detect phase transitions during which the crystallized slurry begins to melt. The graph shows that the three cold slurry compositions with 15% v/v glycerin and soy PC have a progressive phase transition. The graph also shows that the three cold slurry batches having the same composition (15% v/v glycerin and soy PC: traces $B_c$ and $B_m$, $C_c$ and $C_m$, and De and $D_m$) reach equilibrium (as measured by the two thermocouple wire positions) in a similar time frame and at similar temperatures of between about 15° C. and 19° C. depending on the location of the thermocouple (middle/bottom). On the other hand, the cold slurry with a different composition (traces $A_c$ and $A_m$) has a different temperature profile from the other three, reaching an equilibrium sooner at the temperature of between about 15° C. and 19° C. depending on the location of the thermocouple (middle/bottom). FIG. 4 therefore demonstrates that cold slurries of different compositions have different temperature profiles and batch to batch consistency exists across cold slurries having the same composition (e.g., the cold slurries represented by Be and $B_m$, $C_c$ and $C_m$, and $D_c$ and $D_m$ have similar temperature profiles which are different from that of cold slurry represented by $A_c$ and $A_m$).

In certain embodiments, the composition (e.g., in the form of a liquid solution) is packaged into a container. In certain embodiments, the container comprises a sealed container. In certain embodiments, the container may be a syringe, a cannula, a catheter, tubing, and/or a pump, and the like. In some embodiments, the solution is packaged into a syringe and is sealed.

The syringe can be filled sterile (e.g., using aseptic procedures) or the syringe may be pre-filled, sealed, and then terminally sterilized (e.g., using Gamma, E-Beam, EtO, or the like). The composition can also be provided in any other sealed container that can be terminally sterilized, such as a tube used for topical ointment, a cannula, a catheter, and/or a pump, or a larger container used to then fill a plurality of syringes.

In some embodiments, the container is frozen by placing the pre-filled container into a standard freezer, or other cold environment. The temperature of the standard freezer or cold environment at the clinical point of care can be set to a temperature of colder than about −25° C., between about −25° C. and about −20° C., between about −20° C. and about −15° C., between about −15° C. and about −10° C., between −10° C. and about −5° C., between about −5° C. and about 0° C., and warmer than about 0° C. In some embodiments, the temperature is between about −22° C. and −18° C. In some embodiments, the biomaterial is placed into the freezer for a predetermined amount of time such that the temperature of the biomaterial drops to a desired level for forming a cold slurry with a given percentage of ice particles. In some embodiments, the composition is flash-frozen using liquid nitrogen or other liquid cooling methods to speed up the process.

In some embodiments, the biomaterial is turned into a cold slurry through snap freezing. In some embodiments containing lipids, ice particles are created within lipid particles (e.g., liposomes) by a change of pressure. When pure water freezes, it expands. However, starting with specific shapes or sizes of encapsulated water, temperature that is reduced below 0° C. under high pressure conditions cannot freeze until that pressure is released, allowing the water to expand and therefore cause snap freezing of the intraliposomal volume. With snap freezing, a thermal gradient is not required.

In some embodiments, frozen ice particles within lipid particles (e.g., liposomes) is created through a mechanical dispersion method in which sonication is used to create small liposomal vesicles. Lipids are mixed with water and sonicated to make water encapsulated within the lipid particles (e.g., liposomes) and then the resulting mixture is cooled to form ice particles. In some embodiments, the methods disclosed herein allow for the creation of fixed sized lipid particles for various applications of the disclosed emulsion compositions. In some embodiments, sonication during preparation of the lipid particles (e.g., liposomes) is used to limit the size of certain lipids (e.g., phospholipids) to ensure that they will be injectable. Size can also be controlled by creating minimum lamellar size that is energetically favorable and prevents diffusion out of the intraliposomal volume. The free energy barrier of such minimally sized lipid particles will trap water in a setting of higher osmolality outside of the lipid vesicles.

In some embodiments, the final composition is subjected to sterilization and remains sterilized from the point of manufacture and loading into a delivery vessel (e.g., container, bag, or syringe) to the point of administration. In some embodiments, the composition is sterilized during preparation and remains sterilized throughout the entire manufacturing, transportation, and storage process. In some embodiments, the composition is sterilized at the point of care (e.g., using heat, irradiation, high pressure, etc.). In some embodiments, the composition is sterilized while inside of a vessel (e.g., container, bag, or syringe).

In some embodiments, the container is removed from the cold environment (e.g., standard freezer) and immediately injected or applied for therapeutic benefit. In some embodiments, the container is set aside and allowed to warm to an ideal temperature for injection. In one embodiment, there is an indicator for when such temperature is reached. For example, the container may include a visible temperature indicator that can allow for visual monitoring of the temperature of the biomaterial, or the approximate temperature of the biomaterial. The temperature indicator can be a temperature sensing label, sticker, marker, crayon, lacquer, pellet, etc., including reversible temperature labels that can dynamically track temperature changes over time. The temperature indicator can be located inside the container (e.g., a pellet placed directly into the internal solution), on the inside walls of the container, on the outside walls of the container, or in any location that allows for visual tracking of the temperature of the contents inside the container.

After freezing, the syringe or container can be removed from the freezer, cold environment, or other method/device for freezing, and the cold slurry can be immediately injected or applied to a patient (e.g., a human or non-human animal), optionally by topical application site (e.g., directly on a part of the eye, such as the sclera), for therapeutic benefit. In some embodiments, slurry can be applied directly to tissue following invasive surgical methods. In some embodiments, the treatment site may be tissue surrounding nerves, a part of the eye, blood vessels, various organs, and the like. In some embodiments, the syringe is set aside and allowed to warm to an ideal temperature for injection or topical application. The cold slurry can also be removed from the container for a topical application when the container is removed from the freezer, such as by squeezing the container to dispel the cold slurry onto a targeted treatment site. In some embodiments, the cold slurry is in a flowable and/or injectable form immediately after being removed from the freezer without any further mechanical manipulation due to containing a lipid (or other non-water-soluble substance).

In some embodiments, the flowable and/or injectable or topically applied composition contains significant amounts of ice which provides therapeutic benefit for various applications. For example, therapeutic applications of cold slurry are disclosed in U.S. Publication Nos. 2019/0192424, 2019/0183558, and 2022/0079648, the contents of each of which are incorporated by reference in their entireties herein.

In some embodiments, the final product to be administered via injection to a human patient or a subject (such as a human/animal who is not a patient or a non-human animal) is a cold slurry comprised of sterile ice particles of water and varying amounts of excipients/additives, such as freezing point depressants. For example, the percentage of ice particles in the cold slurry can constitute less than about 10% w/w of the slurry, between about 10% w/w and about 20% w/w, between about 20% w/w and about 30% w/w, between about 30% w/w and about 40% w/w, between about 40% w/w and about 60% w/w, more than about 60% w/w, and the like. The sizes of the ice particles will be controlled, optionally by adding lipids, to allow for flowability through a vessel of various sizes (e.g., needle gauge size of between about 7 and about 43). In some embodiments the ice particles are flowable and/or injectable through a needle ranging in diameter from 18 to 22 gauge. In some embodiments, the ice particles are easily flowable and/or injectable through a needle ranging in diameter from 15 to 19 gauge. Vessels of various sizes are described in the '011 Publication, incorporated by reference in its entirety herein. Further, other methods may be used to condition the size of the ice particles to allow for flowability and/or injectability through a vessel of various sizes (e.g., using a filter). In some embodiments, the majority of ice particles have a diameter that is less than about half of the internal diameter of the lumen or vessel used for injection. For example, ice particles can be about 1.5 mm or less in diameter for use with a 3 mm catheter.

The compositions described herein can be used for a variety of applications. After a composition in accordance with some embodiments of the present disclosure has been exposed to freezing temperatures such that it forms a flowable and/or injectable cold slurry, it can be administered topically to an area for therapeutic treatment. Methods of topical administration of cold slurries to the ocular surface are described in U.S. Publication No. 2022/0079648 ("'648 Publication"; U.S. application Ser. No. 17/439,749), incorporated by reference in its entirety herein. The compositions described herein can also be used to form a flowable and/or injectable cold slurry that can be injected into the targeted treatment area for therapeutic effect. Injection methods for cold slurries as described in the '078 Publication, which is incorporated by reference in its entirety herein.

The devices, systems, compositions, and methods disclosed herein are not to be limited in scope to the specific embodiments described herein. Indeed, various modifications of the devices, systems, and methods in addition to those described will become apparent to those of skill in the art from the foregoing description.

EXAMPLES

Example 1—Method of Creating a Cold Slurry Liposome Emulsion Composition

The following describes an example of creating a liposome emulsion composition in accordance with certain embodiments of the present disclosure and the method and process shown in FIG. 2.

A. Materials

- Soy PC (L-α-phosphatidylcholine (95%) (soy), Avanti Lot 5049GUF175
- Chloroform, VWR Lot 19K1656594
- Glycerol, Spectrum Lot 2110091
- 1×PBS, Intermountain Life Sciences, Lot 20903212
- 500 mL round-bottom flask with rubber stopper, Chem-Glass
- 50 mL Falcon tubes, lab stock
- 60 mL syringes, lab stock
- 25G needles, BD
- DI Water
- Dry ice B. Equipment Balance, EQ07052RD Vortex, Fisher, No eq#

Rotary Evaporator, Buchi

Lyophilizer

Hot plate (for water bath)

Ultrasonic bath

Malvern ZetaSizer

C. Procedure a. Soy PC-chloroform solution 1. 3 grams of soy PC were weighed into a 100 mL beaker.
2. 50 mL chloroform was sampled into a graduated cylinder.
3. 3 grams of soy PC (L-α-phosphatidylcholine (95%) (soy PC)) was dissolved in 50 mL chloroform (60 mg/mL) by adding the chloroform into the beaker containing the soy PC. The time to dissolve was recorded.

b. Emulsion Formation Using Water

4. In a 500 mL round bottom flask, 50 mL soy PC solution and 50 mL water were added and vigorously shaken to get a uniform opalescent dispersion. Time of start and end were recorded. The appearance was white, opaque, and visually homogeneous.

c. Extrusion to Form Liposomes

5. Sample was extruded by aspirating in a 60 mL syringe and passing once through a 25G needle. Collection was in a 500 mL round-bottom flask.

d. Rotary Evaporation (Total of 30 Min)

6. The flask was attached to the rotary evaporator and the flask was rotated at a speed of about 150 rpm.

a. RPM Setting: Dial was Set to 2

7. Evaporation occurred under vacuum while the flask was dipped partially in 35° C. water bath for 5 minutes (started at 300 torr and kept observing to detect boiling or foaming. Pressure was gradually released to avoid sample loss until about 200-250 torr was reached).
8. While the vacuum was still on, rotation speed was increased to about 250 rpm and pressure was decreased gradually, allowing for gradual solvent evaporation over about 30 minutes. Boiling was not vigorous. If any excessive boiling or foaming was observed, and the vacuum was momentarily released as needed to prevent sample loss.
9. Steps 3 to 6 took a total of 30 min, at the end of which the vacuum was released and the flask containing about 40 mL of thick suspension was carefully removed.

e. Lyophilization Step

10. The total volume was divided into two fractions, each in a 50-mL glass vials (pre-weighed) (i.e., about 20 mL per vial).
11. The lids were removed and each of the collected vials were covered with Kimwipes, snap-frozen in a dry ice/acetone bath and put into the lyophilizer. Drying was performed overnight (however, in some embodiments, if three or more samples are added, 48 hours will be required).

f. Hydration Step

12. After complete drying (lyophilized pellet appeared like a sponge), the vials were weighed and the weight of the product was noted by subtracting the weight of the vial. Table 1 shows parameters of steps 1 to 12.

TABLE 1

Steps 1-12 of method of creating a liposome emulsion composition

| Temp (° C.) | Ramp (mins) | Hold (mins) | Vacuum (mT) |
|---|---|---|---|
| Freezing | | | |
| −40 | 120 | 600 | |
| Drying step 1-6 | | | |
| −40 | 0 | 30 | 100 |
| −25 | 30 | | 100 |
| −25 | | 720 | 100 |
| −25 | | 720 | 100 |
| −25 | | 720 | 100 |
| 20 | 500 | | 100 |
| Dying step 7-12 | | | |
| 20 | | 720 | 100 |
| 20 | | Hold | 100 |

13. The weight of the two fractions (collectively one batch) were about 3 gm (recovery was almost 100%).
14. 6 mL of water was added to one of the tubes and vigorously vortexed. It was then transferred to the other tube and vigorously vortexed. The pipette tip was used to disperse lumps.
15. The tube was incubated in a 37° C. water bath for 10 minutes followed by bath sonication for 10 minutes.
16. Water was added to reach a total of 10 mL (approximately 7 mL total was needed, where the lipids constituted about 3 mL of the mixture). This yielded a 0.3 g/mL lipid concentration.
17. To this volume, 1.4 mL glycerol was added, which yielded: 0.26 g/mL lipid, total volume of about 11.4 mL and 12% systemic glycerol concentration. In some embodiments, the trapped volume of this suspension is in the range of 41% v/v to 48% v/v.
18. Measure particle size and zeta potential
    a. Particle size and zeta potential were measured at time=0 (when the product was made)
    b. Zeta potential analysis result at time=0
19. Submit to AS if needed.
20. One vial was stored at room temperature. Second vial was stored at 2° C. to 8° C.
21. Particle size and zeta potential analysis were repeated after two weeks.

What is claimed is:

1. A composition comprising:

an amount of water;

a non-water-soluble substance; and a first excipient, wherein the composition is configured to form a flowable ice slurry when exposed to freezing temperatures;

wherein the non-water-soluble substance is a lipid;

wherein the lipid is L-α-phosphatidylcholine (soy PC); and wherein the concentration of the soy PC in the composition is about 0.26 g/mL.

2. The composition of claim 1, wherein the composition comprises a plurality of lipids.

3. The composition of claim 2, wherein the composition comprises a lipid particle, and wherein the lipid particle comprises the plurality of lipids.

4. The composition of claim 3, wherein the first excipient is configured to pass through a lipid bilayer of the lipid particle.

5. The composition of claim 4, wherein a first solution encapsulated within the lipid particle and a second solution outside of the lipid particle are substantially equal in composition.

6. The composition of claim 3, wherein the lipid particle is a liposome or a micelle.

7. The composition of claim 1, further comprising a phospholipid selected from the group consisting of 1,2-distearoyl-sn-glycero-3-phosphocholine (DSPC), egg sphingomyelin (DPSM), dipalmitoylphosphatidyl choline (DPPC), dicethylphosphate (DCP), phosphatidylethanolamine (PE), phosphatidylserine (PS), phosphatidylglycerol (PG), and a combination thereof.

8. The composition of claim 1, wherein the first excipient is selected from the group consisting of a salt, an ion, Lactated Ringer's solution, a sugar, a biocompatible surfactant, a polyol, and a combination thereof.

9. The composition of claim 1, wherein an average freezing point of a total volume of the composition is between about −25° C. and about −5° C.

10. A method of preparing a cold slurry for administration to a patient at a clinical point of care, the method comprising:

preparing a composition comprising a plurality of lipid particles;

adding an excipient to the composition, wherein the excipient is configured to reduce the freezing point of a volume external to the plurality of lipid particles and of a volume internal to the plurality of lipid particles; and cooling the composition to a predetermined temperature such that the cold slurry is formed, wherein the cold slurry comprises a plurality of ice particles;

wherein the plurality of lipid particles comprises L-α-phosphatidylcholine (soy PC); and wherein the concentration of the soy PC in the composition is about 0.26 g/mL.

11. The method of claim 10, wherein the volume internal to the lipid particles is between about 20% and 50% of a total volume of the composition.

12. The method of claim 10, wherein a first solution comprising the volume internal to the plurality of lipid particles and a second solution comprising the volume external to the plurality of lipid particles are substantially equal in composition.

13. The method of claim 10, wherein the composition comprises a liposome or a micelle, and wherein the liposome or the micelle comprises the plurality of lipid particles.

14. The method of claim 10, wherein the plurality of lipid particles further comprises a phospholipid selected from the group consisting of 1,2-distearoyl-sn-glycero-3-phosphocholine (DSPC), egg sphingomyelin (DPSM), dipalmitoylphosphatidyl choline (DPPC), dicethylphosphate (DCP), phosphatidylethanolamine (PE), phosphatidylserine (PS), phosphatidylglycerol (PG), and a combination thereof.

15. The method of claim 10, wherein the excipient is selected from the group consisting of a salt, an ion, Lactated Ringer's solution, a sugar, a biocompatible surfactant, a polyol, and a combination thereof.

* * * * *